United States Patent [19]
Chen

[11] Patent Number: 5,464,415
[45] Date of Patent: Nov. 7, 1995

[54] SUTURELESS INTESTINAL ANASTOMOSIS GUN

[76] Inventor: Te-Chuan Chen, No. 4-1, Lane 131, Sec. 1, Hang Chou S. Road, Taipei, Taiwan

[21] Appl. No.: 213,130

[22] Filed: Mar. 15, 1994

[51] Int. Cl.⁶ ............................................. A61B 17/00
[52] U.S. Cl. ............................................. 606/153; 606/154
[58] Field of Search .............................. 606/153–156, 606/148, 150; 623/1, 12; 227/175, 179, 181, 19

[56] References Cited

U.S. PATENT DOCUMENTS

| | | | |
|---|---|---|---|
| 4,667,673 | 5/1987 | Li | 606/153 |
| 4,957,499 | 9/1990 | Lipatov et al. | 606/153 |
| 5,282,810 | 2/1994 | Allen et al. | 606/153 |

FOREIGN PATENT DOCUMENTS

WO87/06448  11/1987  WIPO ................. 606/153

*Primary Examiner*—Tamara L. Graysay
*Assistant Examiner*—Jeffrey A. Schmidt
*Attorney, Agent, or Firm*—Davis Hoxie Faithfull & Hapgood

[57] ABSTRACT

Directing to the difficulties involved in the deep rectal surgery, the present invention relates to a sutureless intestinal anatomosis gun which facilitates the rectal surgery to be performed by entering through the anus and protruding out from the upper end of rectum so as to install an anastomosis ring that has been connected to the intestine for anastomosis of the rectum, comprising a plurality of tubes, an anastomosis ring seat, a fixed shaft, a screw rod and a nut. During the operation of intestinal anastomosis, the inner sleeve and the anastomosis ring seat can be driven in sequence by means of the nut and the screw rod such that the end of the rectum is pushed precisely to enter into the gap of the anastomosis ring and then the anastomosis ring is precisely closed. Thereafter, the anastomosis ring seat and the anastomosis ring are disengaged and then the said anastomosis gun is removed to complete the intestinal anastomosis.

1 Claim, 14 Drawing Sheets

SUTURELESS INTESTINAL ANASTOMOSIS GUN

BACKGROUND OF THE INVENTION

Introduction

Biofragmentable anastomosis rings (hereinafter referred to as BAR) developed by David & Geck, American Cyanamid Company, Danbury, Conn. 06810 have begun to be used for sutureless intestinal anastomosis in recent years because they are simple, fast and safe to operate and capable of being fragmented and to pass out of the body in two to three weeks and so far there are a number of articles relating to the use of the BAR published in medical journals. The BAR was first introduced into Taiwan in 1992 by the applicant for use on patients with diseases of the large intestine or rectum in the Surgical Department, of Taipei Municipal Jen Ai Hospital, Taipei, Taiwan, and found to be highly recommendable for general application because of the excellent results that have been observed just as what were reported in the referenced literatures from abroad.

Background of Studies (Reasons, Motives, Objects and Importance)

In the intestinal surgeries within the shallow wide abdominal cavity, the BAR can be easily operated for use by means of only fingers of simple operating instruments, but they can hardly be operated directly by hands to perform intestinal anastomosis for surgical treatment on diseases of the rectum, such as cancer of the rectum, within the deep and narrow pelvic cavity. In view of the fact that the occurrence of the rectal cancers have been sharply increased and the rectal cancer has become one of the major causes of death in recent years in our country (Taiwan, ROC), the number of the rectal surgeries has been increased. Moreover, with the extended life expectancy, there are now many patients who are older when the operation is performed. Therefore, to the benefit of more patients, there is an urgent need for developing a simple and reliable operating method to be performed in reduced time such that the BARs with their high efficacy can be well suited for application in the rectal surgeries within the deep and narrow pelvic cavity.

SUMMARY OF THE INVENTION

In view of the above restrictions, efforts have been devoted to the investigations, trials and experiments and, after repeated improvements, the sutureless anastomosis gun for the biofragmentable anastomosis ring of the present invention has been finally developed.

The object of the present invention is to provide a said anastomosis gun for use in sutureless anastomosis of the intestine or rectum near the anus. The said anastomosis gun of the present invention comprises a plurality of tubes, an anastomosis ring seat, a fixed shaft, a screw rod and a nut. During intestinal anastomosis, the inner sleeve and the anastomosis ring seat can be driven in sequence by means of the nut and the screw rod such that the end of the rectum is pushed precisely to enter into the gap of the anastomosis ring and then the anastomosis ring is exactly closed. Thereafter, the anastomosis ring seat and the anastomosis ring are disengaged and then the said anastomosis gun is removed to accomplish the intestinal and rectal anastomosis.

BRIEF DESCRIPTION OF THE DRAWINGS

To achieve the above object, the technical means employed in the present invention and the effects thereof will be described in detail by way of an embodiment taken in conjunction with the accompanying drawings, in which:

FIG. 10 is a cross section view showing the condition when the BAR is snapped on;

FIG. 11 is a schematic view showing the condition when the BAR is snapped on;

FIG. 13 is a schematic view showing the BAR seat being pushed further down so as to disengage from the BAR after the BAR has been snapped on.

DETAILED DESCRIPTION OF THE PREFERRED EMBODIMENT

Figure 1:
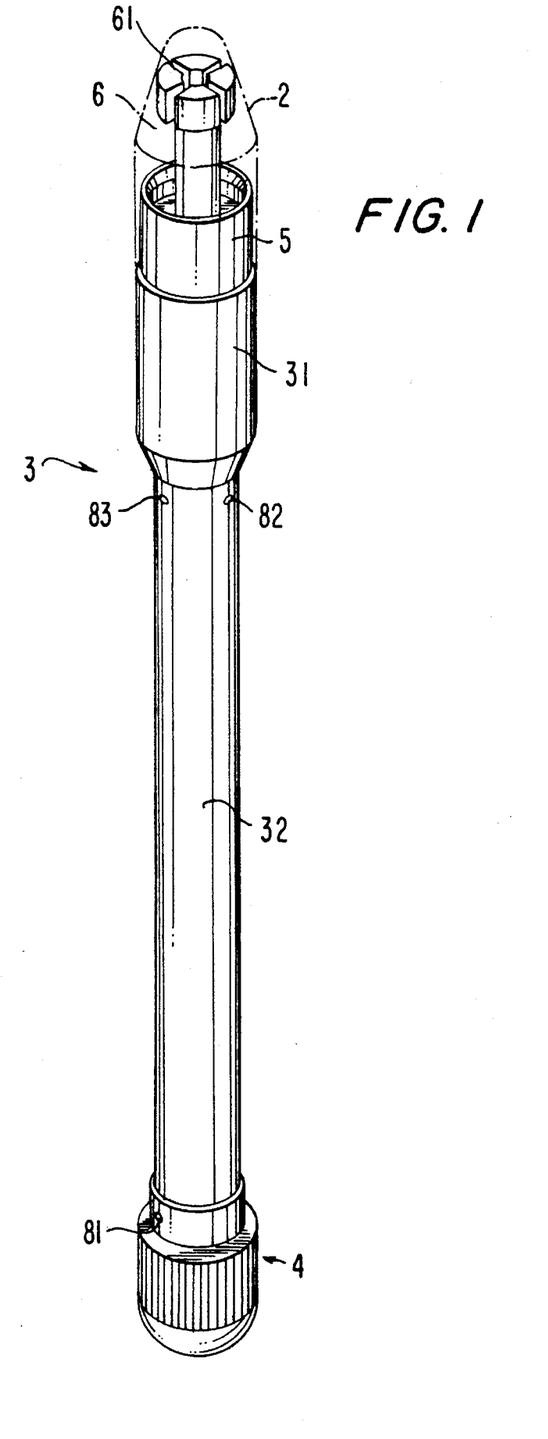
FIG. 1 is a perspective view showing an embodiment of the present invention.

Referring to FIG. 1, there is a perspective view of an embodiment of the present invention. The said anastomosis gun according to the present invention is formed in the shape of a round rod having both ends in a larger diameter. A lining tube 5 is fitted in an outer tube 31 at one end with an anastomosis ring seat 6 installed in the lining tube 5, the front end being fitted with a guide head 2 to facilitate insertion. The other end is in the shape of a round smooth nut 4 which is retained at the rear end for rotation by means of a pair of screws 81.

Figure 2:
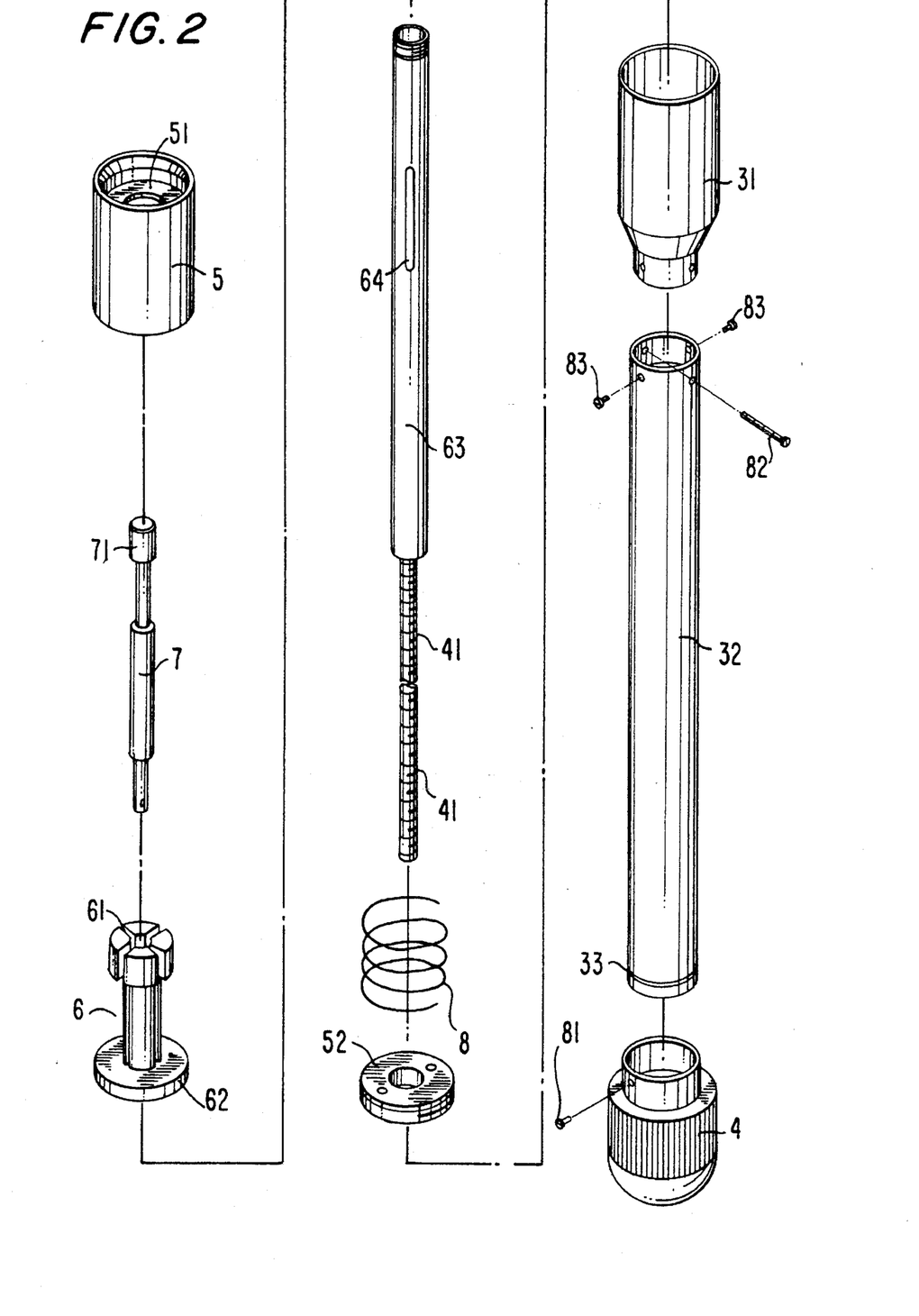
FIG. 2 is an exploded view showing an embodiment of the present invention.

Referring to FIG. 2, there is an exploded perspective view showing an embodiment of the present invention. The sutureless intestinal anastomosis gun according to the present invention is comprised, in its essentials, of a guide head 2, a housing 3, a nut 4, a lining tube 5, an anastomosis ring seat 6, a movable shaft 63, a fixed shaft 7, a spring 8 and screws 81 wherein the guide head 2 is in the shape of a smooth conic cover; the housing 3 is comprised primarily of an outer tube 31 of a larger diameter connecting at the rear side with an elongated tube body 32; the nut 4 has a rear end formed into a smooth spherical faced round body which is provided in the center with a threaded hole; one end of the lining tube 5 is formed with a stop edge 51 at an appropriate distance from the end face, a filler plate 52 being threaded to the other end thereof; the anastomosis ring seat 6 has the lower end formed into a flange 62 with the upper end being divided into several segments by the same number of crossed grooves 61; the movable shaft 63 is provided with an elongate slit 64, both ends thereof being formed with male and female threads, respectively; and the spring 8 is a spiral compression spring.

Figure 3:
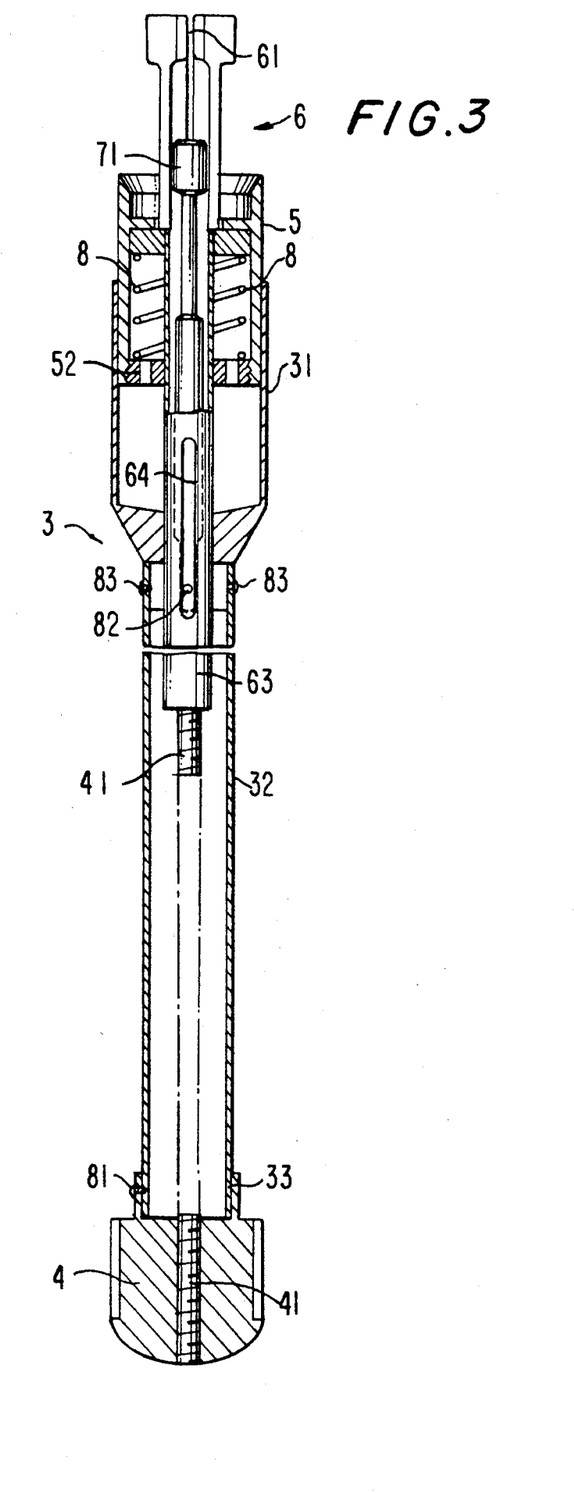
FIG. 3 is a cross section view showing an embodiment of the present invention.

When assembling, the movable shaft 63 is first threaded to a screw rod 41 and then fitted in the tube body 32 together with the fixed shaft 7 by means of a screw 82. The nut 4 is fitted at the rear end of the tube body 32 by a pair of screws 81 mating with a retaining groove 33. The front end of the tube body 32 is connected to the outer tube 31 by means of the screws 83. The end of the anastomosis ring seat 6 having a smaller diameter is placed in the lining tube 5, followed by the spring 8, and then both are restricted within the lining tube 5 by the filler plate 52. Finally, the lining tube 5 is placed into the outer tube 31, causing the movable shaft 63 to extend through the filler plate 52 to be threaded to the anastomosis ring seat 6, and the fixed shaft 7 to extend through the filler plate 52 into the anastomosis ring seat 6, thus completing the assembly into the relationship as shown in FIG. 3. Since the movable shaft 63 is connected to the screw rod 41 and restricted in the tube body 32 together with the fixed shaft 7 by means of the screws 82 fitting in the elongate slit 64, the anastomosis ring seat 6 can be actuated to move linearly by the movable shaft 63 by rotating the nut 4. Moreover, since a compression spring is placed in the lining tube 5 between the filler plate 52 and the anastomosis ring seat 6, the lining tube 5 and the anastomosis ring seat 6 are retracted at the same time during actual operation, and then the anastomosis ring seat 6 alone is retracted inwardly after the lining tube 5 has been retracted to the bottom, thereby resulting in the relative movement between the lining tube 5 and the outer tube 31, and then the movement of the anastomosis ring seat 6 relative to the lining tube 5.

Figure 4:
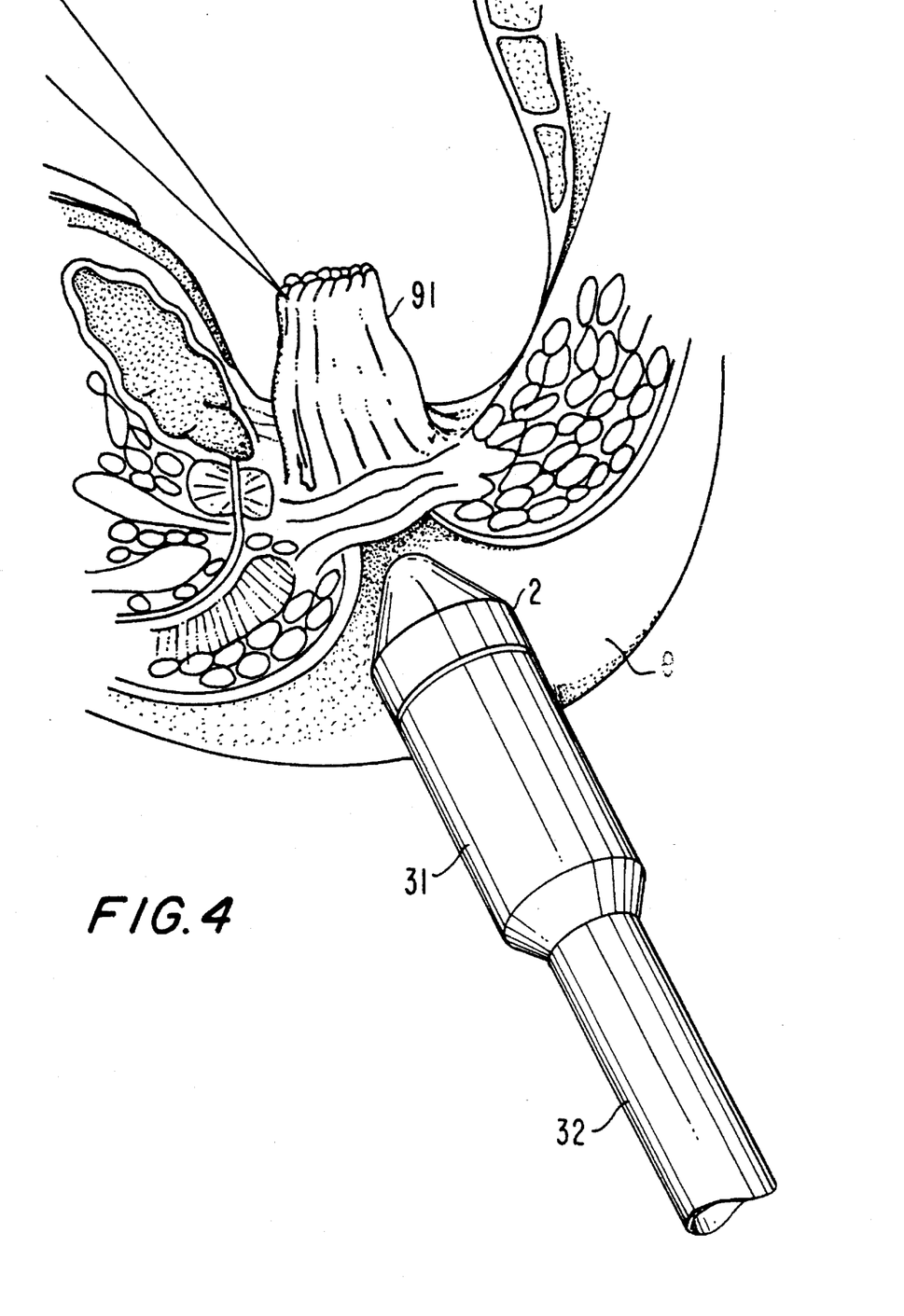
FIG. 4 is a view showing the condition when the said anastomosis gun of the present invention is ready for insertion after begin fitted with a guide head.
Figure 5:
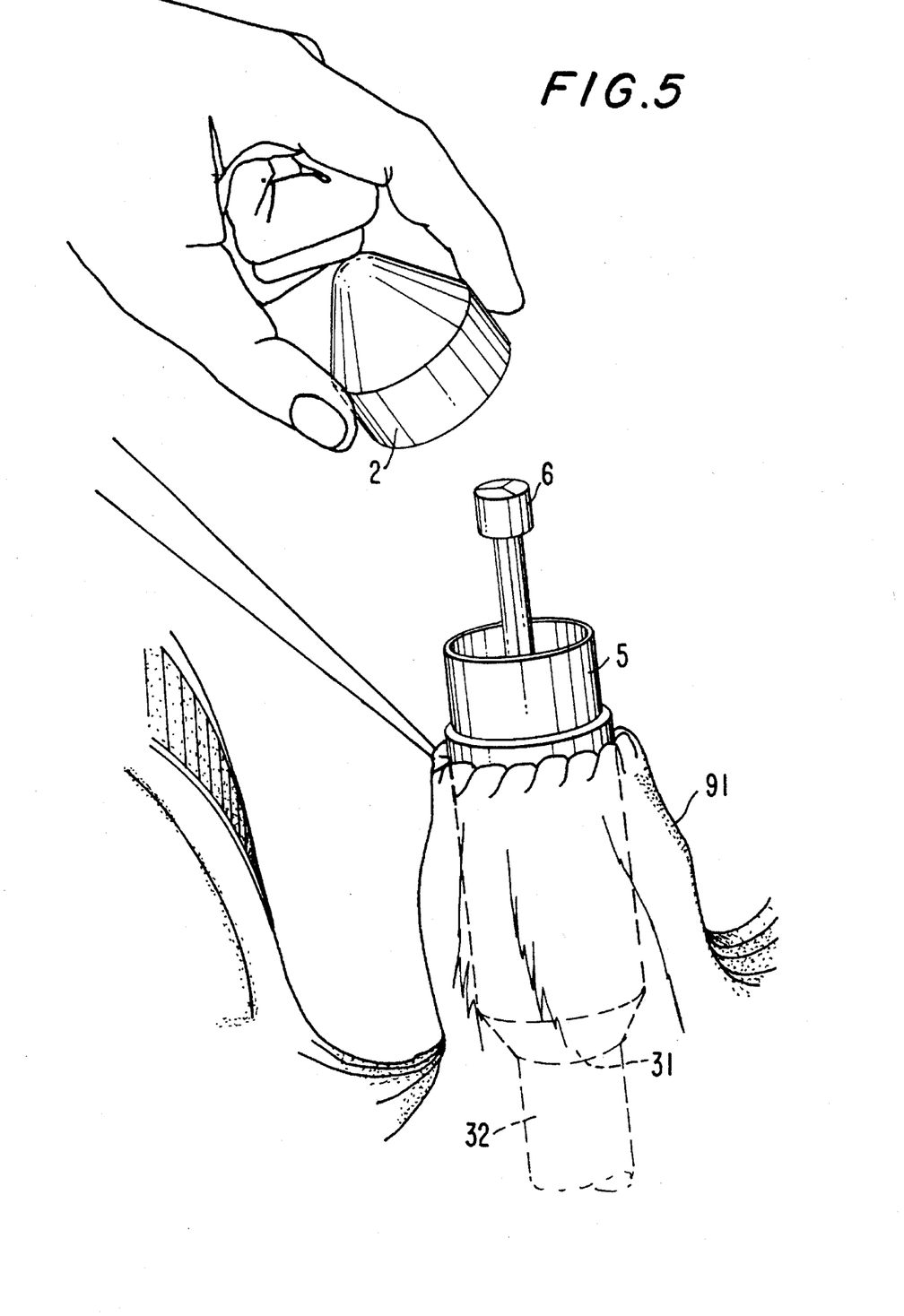
FIG. 5 is a view showing the condition when the guide head is removed after insertion of the said anastomosis gun trough the rectal end.
Figure 7:
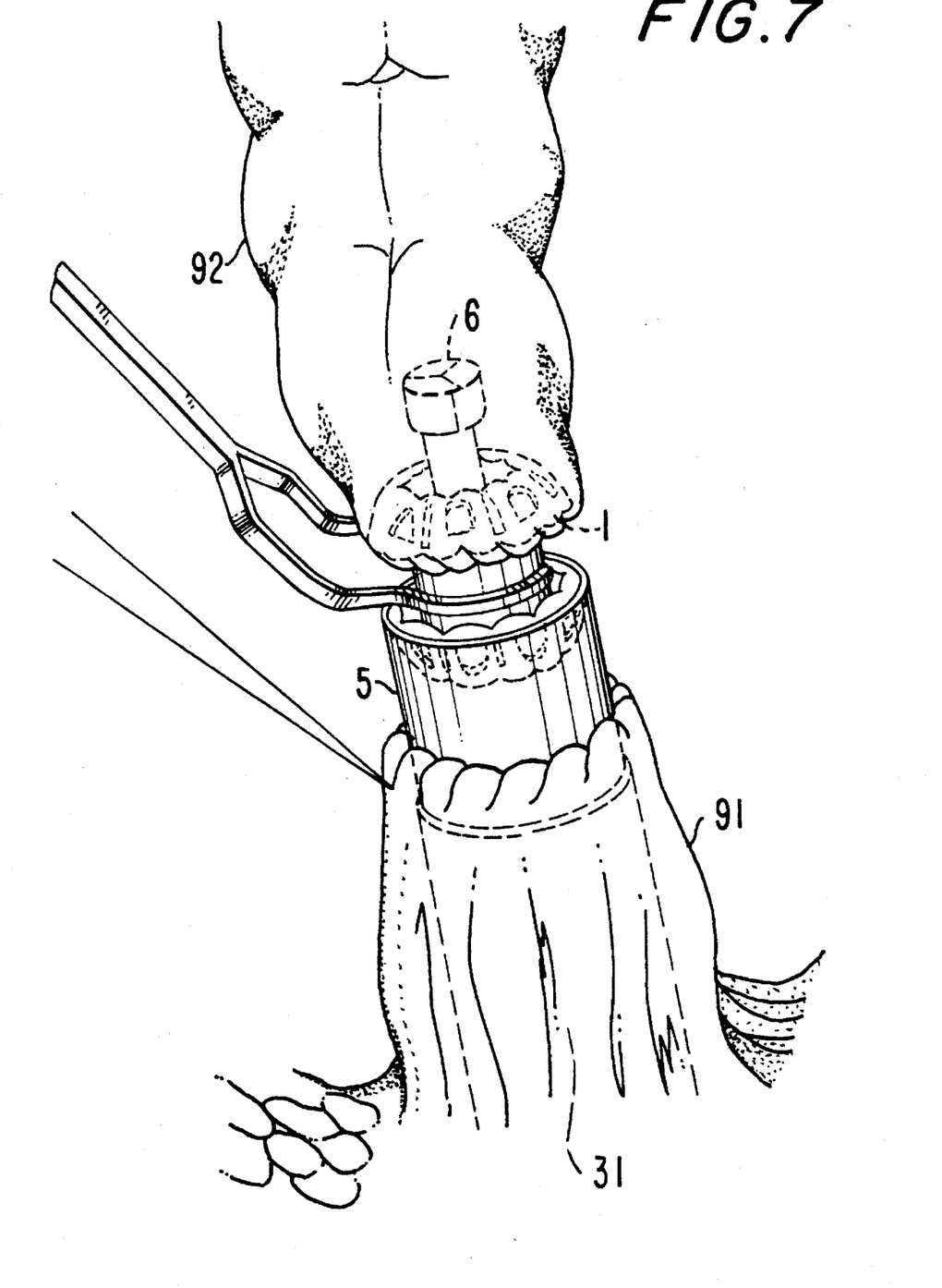
FIG. 7 is a schematic view showing a BAR which has been connected to the end of the large intestine being fitted over the said anastomosis gun.
Figure 8:
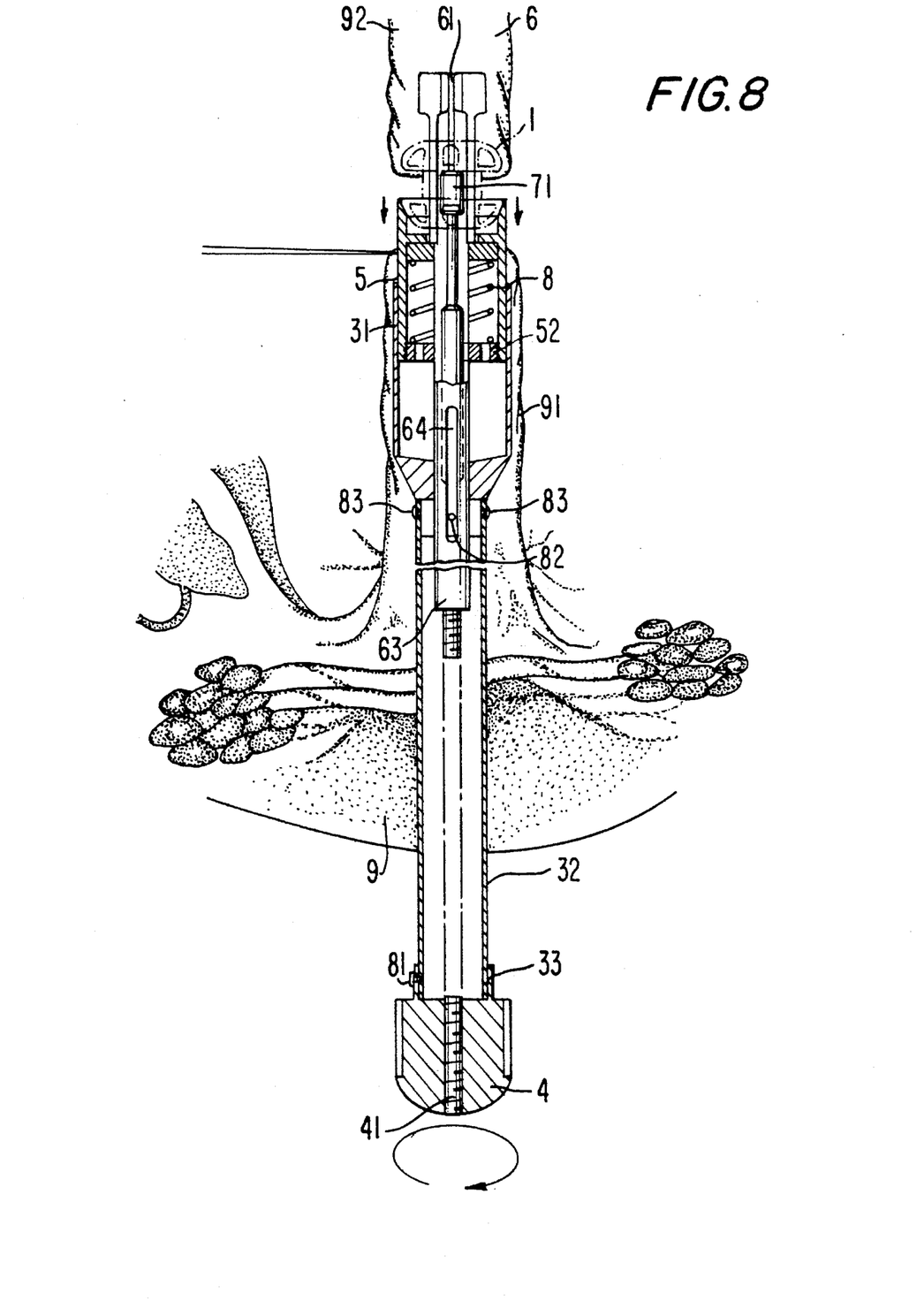
FIG. 8 is cross section view showing the BAR being fitted over the said anastomosis gun.
Figure 9:
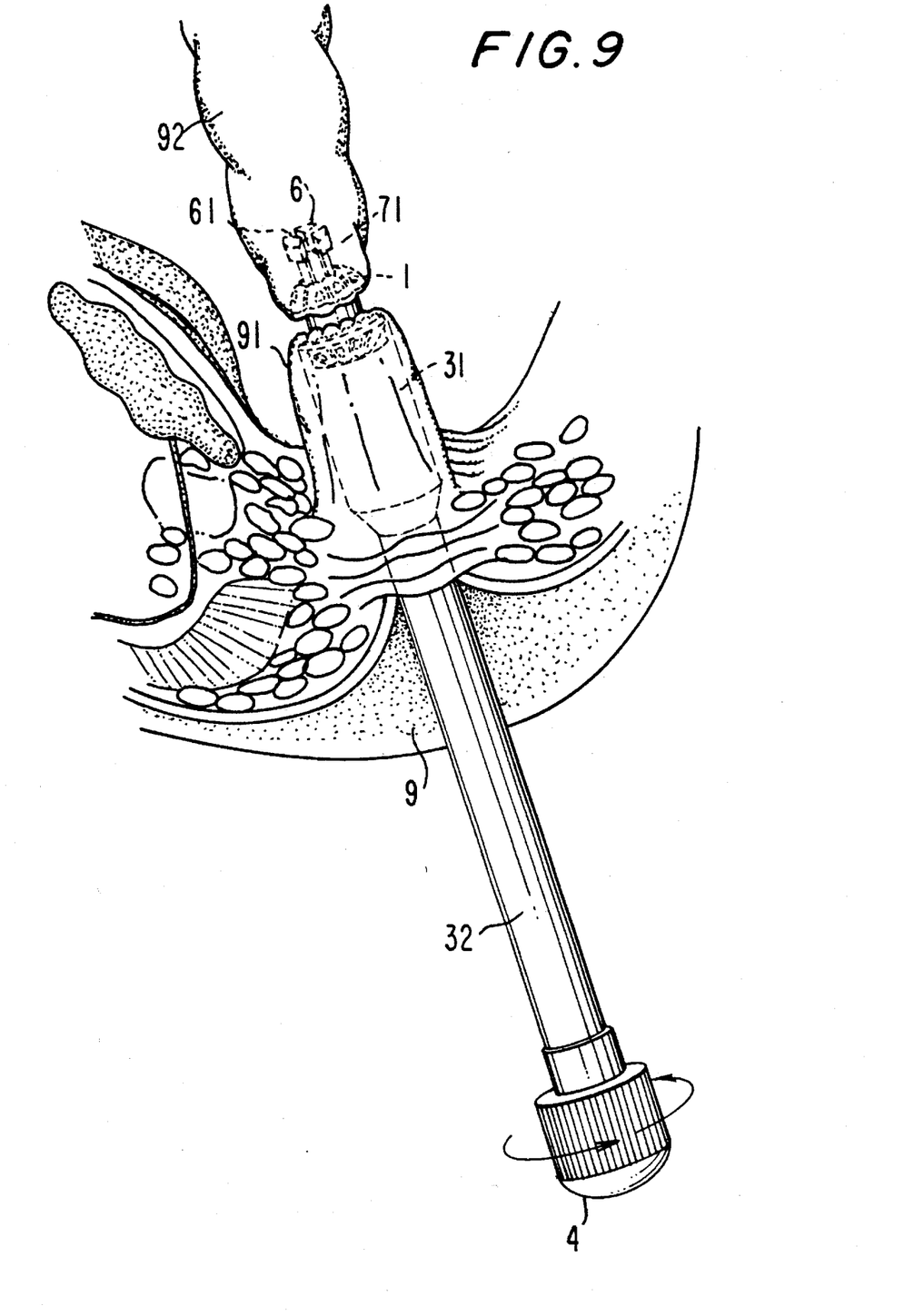
FIG. 9 is a schematic view showing the opening of the rectum being pushed into the gap of the BAR by rotating a nut in a clockwise direction.
Figure 10:
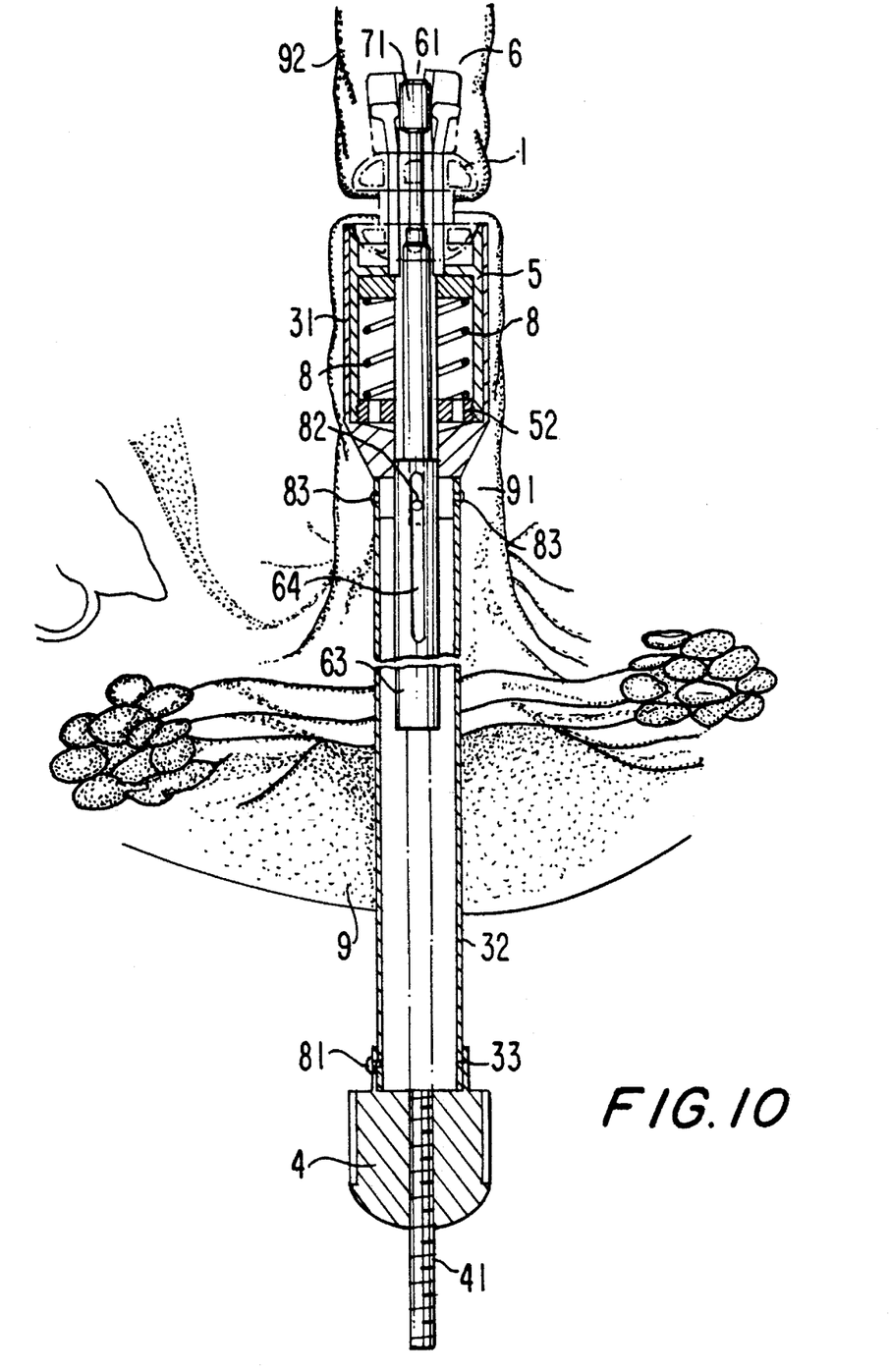
Figure 11:
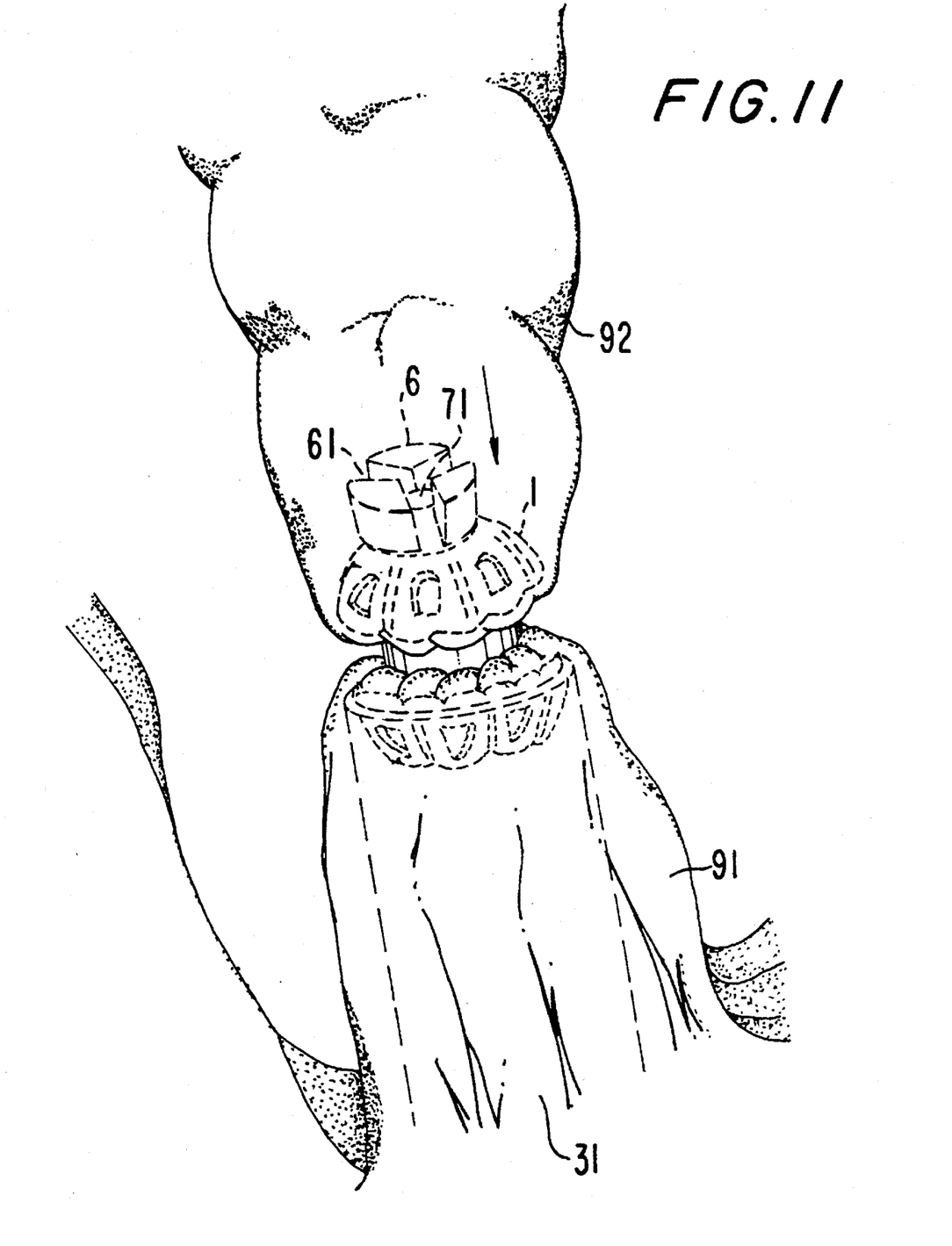
Figure 12:
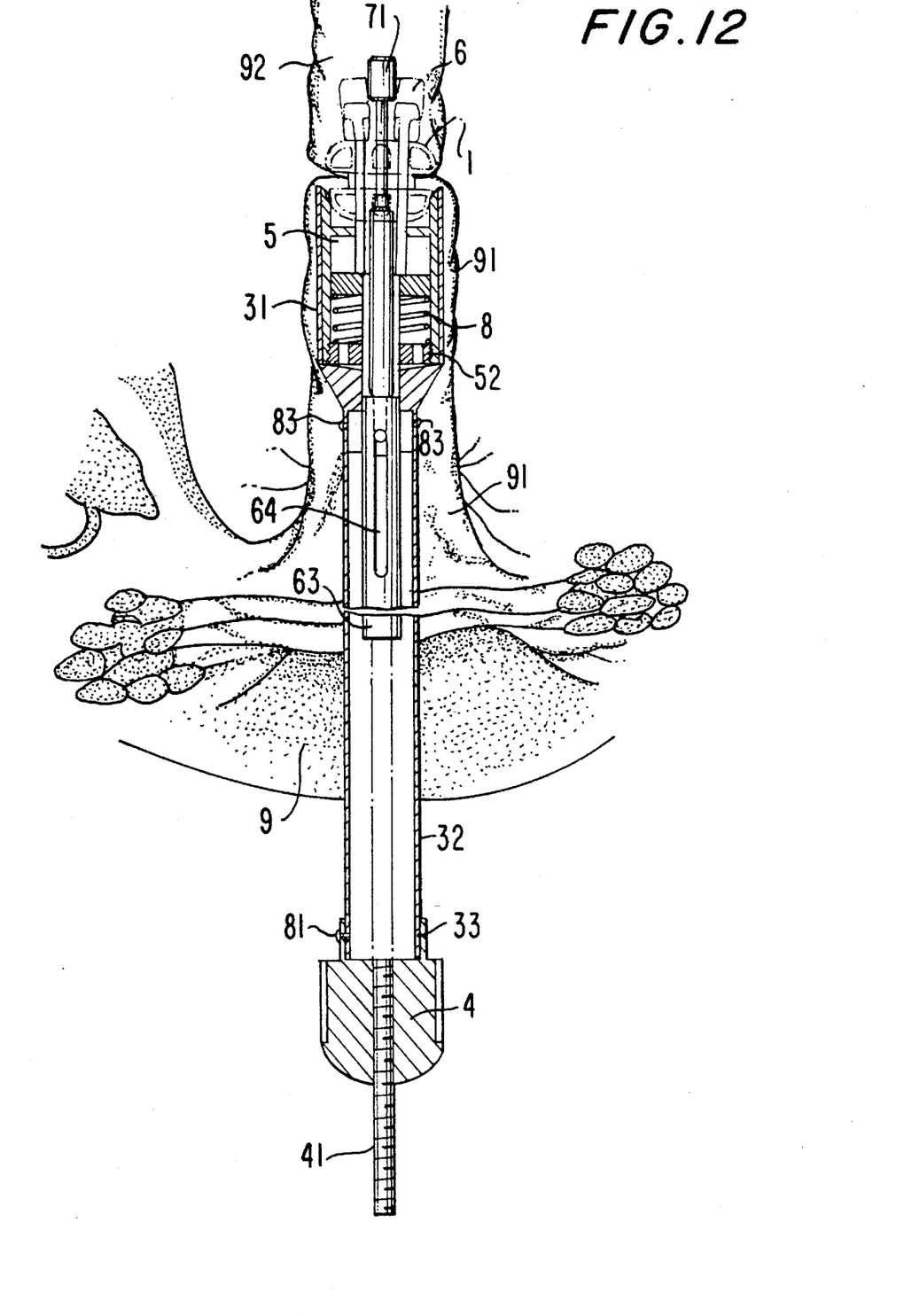
FIG. 12 is a schematic view showing the condition after the BAR is closed completely.
Figure 13:
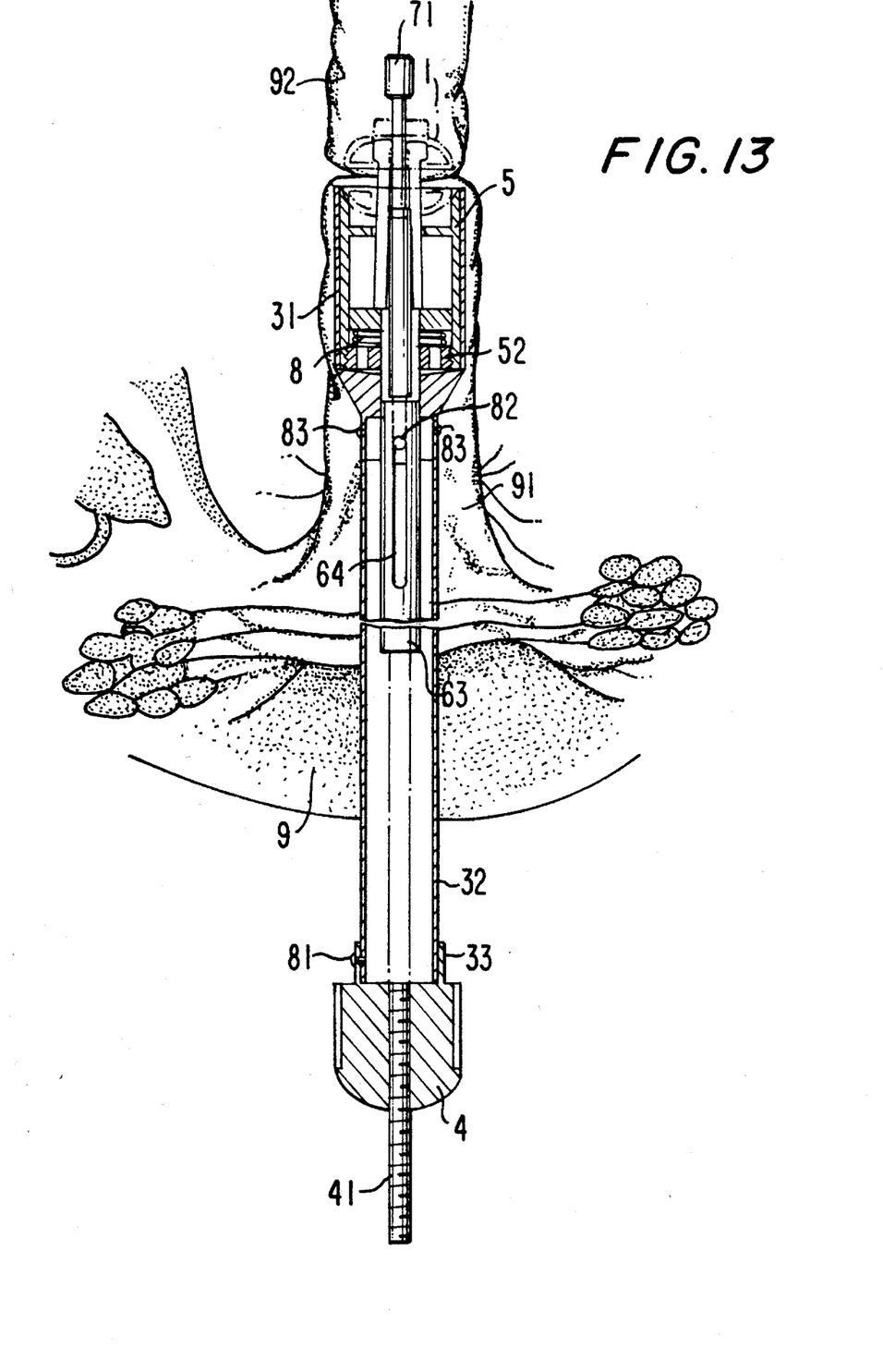
Figure 14:
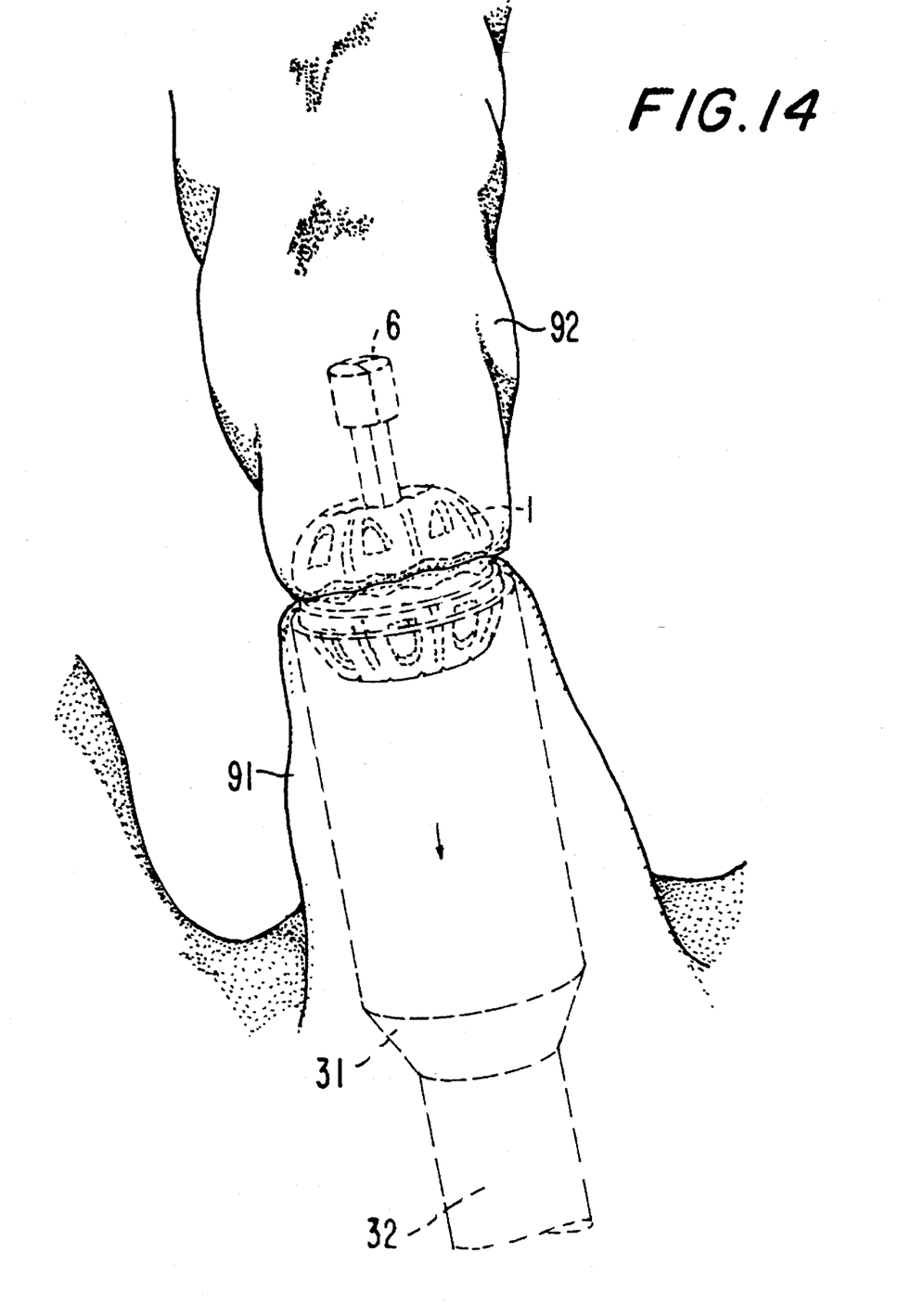
FIG. 14 is a schematic view showing the BAR seat being pushed back upwardly to its initial position for removal after the BAR has been closed.

In the embodiment of the present invention, the actual operation is performed by first removing the diseased portion of the intestine and having the intestinal ends threaded with purse-string sutures. Then the anastomosis ring 1 is tied to the end of the intestine 92, and then the said anastomosis gun is properly adjusted for mounting the guide head 2, the said anastomosis gun being inserted from the anus 9, then passing through the rectum 91 and out from the upper end of the rectum 91 for mounting the anastomosis ring 1 as shown in FIG. 4. Then the guide head 2 is removed as shown in FIG. 5 and the open end of the rectum 91 is properly tied to the lining tube 5 of the said anastomosis gun as shown FIG. 6, and the anastomosis ring 1 which has been connected to the intestine 92 is fitted over the anastomosis ring seat 6 in the condition as shown in FIG. 7. Then the nut 4 is rotated in a clockwise direction as shown in FIG. 8, urging the screw rod 41 to pull the movable shaft 63, the anastomosis ring seat 6, the spring 8, the filler plate 52, and the lining tube 5 to move down, thus causing the lining tube 5 to be retracted relative to the outer tube 31 and the open end of the rectum 91 such that the open end of the rectum 91 is introduced precisely by pushing the edge of the outer tube 31 into the gap of the anastomosis ring 1 as shown in FIG. 9. Continued rotation of the nut 4, after the end of the rectum 91 has been tied as shown in FIG. 10, will no longer move the lining tube 5 because the lower end thereof abuts against the bottom of the outer tube 31, and only the movable shaft 63 pulling the anastomosis ring 6 will move down relative to the fixed shaft 7 and the lining tube 5. When the anastomosis ring seat 6 is moved down into a proper position, the upper end thereof is spread out by the restricting head 71 on the upper end of the fixed shaft 7 such that the anastomosis ring 1 is retained as shown in FIG. 11 and snapped into the closed condition as shown in FIG. 12. After the anastomosis ring 1 is fastened, the said anastomosis gun is disengaged from the anastomosis ring 1 and removed, thus to complete intesinal anastomosis. The said anastomosis gun can be disengaged from the anastomosis ring 1 in two ways. As shown in FIG. 13, the said anastomosis gun can be disengaged from the anastomosis ring 1 by moving the anastomosis ring seat 6 further down to pass through the anastomosis ring 1 by rotating the nut in a clockwise direction after it is closed. Alternatively, after the anastomosis ring 1 is closed, rotate the nut in a counterclockwise direction to move the anastomosis ring seat 6 upwardly and back to the position where it is initially fitted into the anastomosis ring 1 as shown in FIG. 14, then the said anastomosis gun can be pulled straight down and disengaged from the ring.

METHOD AND STEPS FOR STUDY

Using the BAR for anastomosis of the rectum is extremely difficult in the deep and narrow pelvic cavity. Under such circumstances, it is initially visualized to study and design a suitable auxiliary device for use in combination with the BAR for performing the intestinal anastomosis. It is much like that the BAR is a bullet and the auxiliary device is a gun and the desired results can only be obtained by using both in cooperation. Therefore, the following methods and steps were used and taken in the study:

1. Thorough understanding of the properties of the BAR: Efforts have been directed to making references to academic papers relating to the BAR, collecting related data from the manufacturer, and analyzing samples of the BAR.

2. Initial layouts were drawn after repeated thinking, visualization, making simple drawings, analysis, computer aided drawings, computer simulated operation, trial, and feasibility review. Based on the layout and after a number of modifications, a prototype of the device was made by using various working machines such as a precision lathe and milling machine to make metal and plastic members. During the process, the difficulties encountered and the solutions are as follows:

(1) How to transpose the combined body of the opening on the lower end of the intestine and the BAR to the opening on the upper end of the rectum in a deep and narrow pelvic cavity:

A metal tube of suitable size (having the same diameter as the rectum) is used which is inserted from the anus and extending out from the opening on the upper end of the rectum. Then the combined BAR body is placed on the opening of the metal tube by fingers followed by moving the top opening of the rectum to the BAR.

Figure 6:
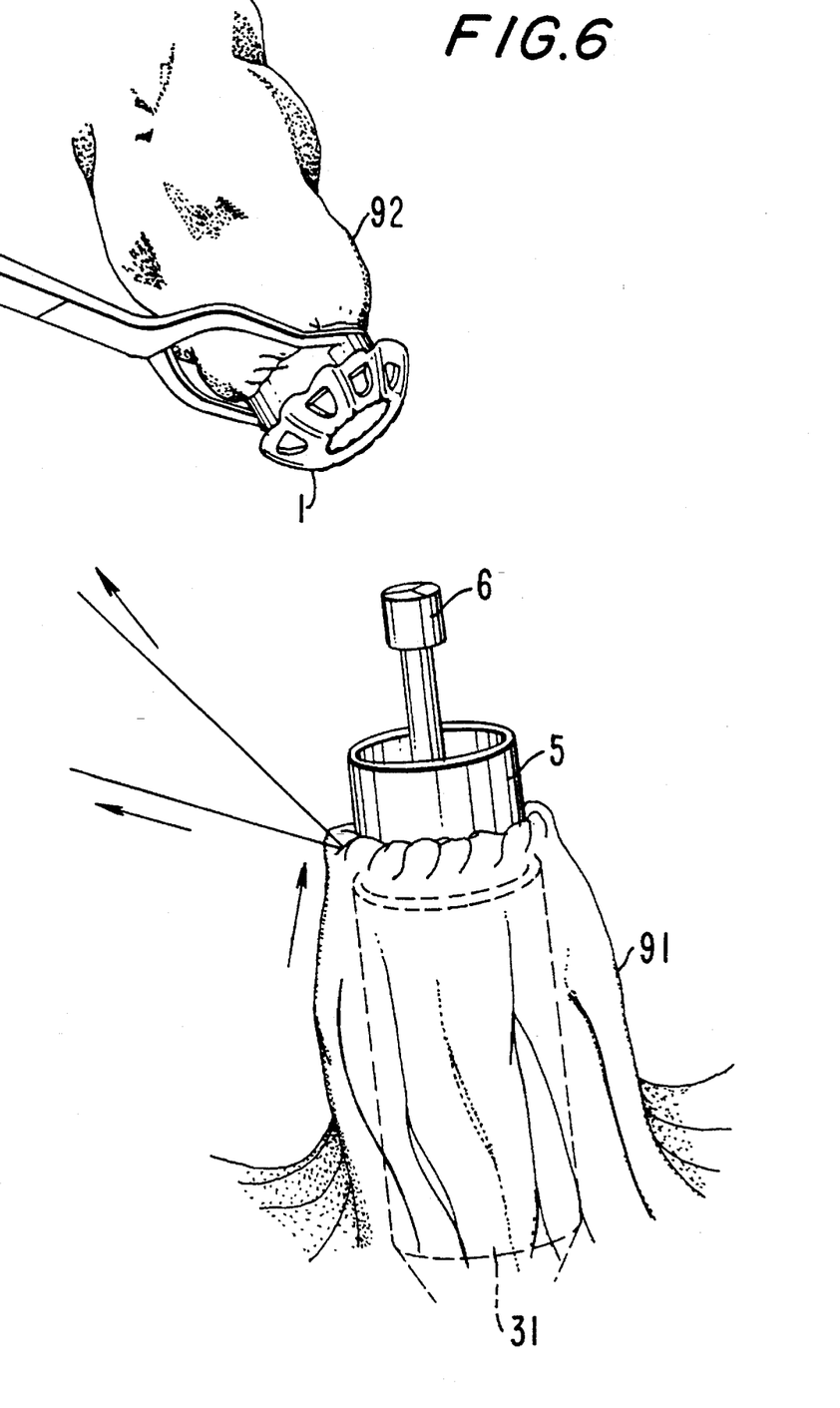
FIG. 6 is a schematic view showing the end of the rectum being properly tied to the tube body.

(2) How to tightly tie the purse-string suture of the rectal opening in the gap of the BAR:

The purse-string suture of the rectal opening is sutured and suitably tied to the inner tube by means of the related movement in position between the openings of the mutually slidable outer and inner tubes (see FIG. 6). Then the opening of the rectum is precisely pushed into the gap of the BAR via the end edge of the outer tube opening and then tightly tied (see FIG. 10).

(3) How to close the BAR to secure in the lumen of the intestine without damaging the intestinal wall:

Originally, the BAR had to be snapped to secure it by compressing the intestinal wall and the BAR with fingers, such that the soft frangible intestinal wall was frequently injured, resulting in hematoma or even rupture, due to squeezing in the BAR. The only solution to prevention of injuries of the intestinal wall is to directly snap the BAR to secure it by applying opposite forces on both sides in the intestine. To this end, various models have been made in trials after repeated scrutiny, actual drawing and computer simulated tests, which are then subject to experiments and actual tests, and finally the said anastomosis gun of the present invention has been designed comprising an anastomosis ring 6, a lining tube 5, a filler plate 52, a compression spring 8, a fixed shaft 7, a rotatable nut 4, a movable shaft 63, etc as elaborated hereinbefore. With the said anastomosis gun of the present invention, the anastomosis ring can be simply snapped to secure it by rotating the nut clockwise, thus to complete the intestinal anastomosis.

(4) How to test and evaluate the function of the said anastomosis gun of the present invention:

1. The movements of the various components are repeatedly tested after they were disassembled.

2. Coordinated movement of the said anastomosis gun was tested after it had been integrally assembled.

3. The essential requirements for high pressure sterilization such the endurance, resistance to force, temperature, and pressure of the above movements were tested.

4. Simulated intestines (tubular foam rubbers), intestines from animals (pigs), and large intestines from humans (operation specimen of intestine) were repeatedly tested.

(5) Evaluation of the results:

After numerous successful tests, the said anastomosis gun of the present invention was used for the first operation in Taipei Municipal Jen Ai Hospital, Taipei, Taiwan on Oct. 14, 1993. The operation was performed perfectly in which the large intestine and lower rectum was anastomosed sucessfully for a victim of rectal cancer (Mr. Lin Yin-tang, male, age 42, Registration No. 1229119). The patient was discharged uneventfully on Oct. 19, 1993.

1. Early results: There were a number of disadvantages with the earlier models which were inconvenient to operate and inaccurate in mechanical movement due to their simple and crude structures. Therefore, the construction and function of the earlier models have not yet been publicized and only the results of the clinical applications had been briefly reported.

2. Latest results: With the attention and encouragement by medical experts from abroad, further efforts have been directed to continued research and development. After a number of tests externally and trials internally of the body, modifications have been made to a great extent to completely overcome the disadvantages and defects with the earlier models, thereby to obtain the said anastomosis gun of the present invention which can actually be used for application on human bodies. Heretofore, the said anastomosis gun of the present invention has been used in combination with the BAR for the anastomosis of the lower rectum with the large intestine on eight patients. Among them the seventh patient is a senior of age 100, and with the fifth patient, anastomosis was performed with the BAR at the distance one cm from the anus, both cases being new world records.

From the foregoing, the said anastomosis gun can be operated by rotating a nut at one end, the end of the rectum can be pushed exactly to the gap of a BAR, causing the BAR to be snapped exactly to secure it at the other end and the said anastomosis gun can be disengaged from the BAR, such that during deep rectal anastomosis, the said anastomosis gun can be inserted into the anal canal and protruded out from the upper end of the rectum to fit with the BAR of the intestine for rectal anastomosis, thus to overcome the space limitation of pelvic cavity, thereby enabling the patients to avoid the misery from the artificial anus.

| LIST OF REFERENCE NUMBERS | |
| --- | --- |
| 1 anastomosis ring | 41 screw rod |
| 2 guide head | 51 stop edge |
| 3 housing | 52 filler plate |
| 4 nut | 61 groove |
| 5 lining tube | 62 flange |
| 6 anastomosis ring seat | 63 movable shaft |
| 7 fixed shaft | 64 elongate slit |
| 8 spring | 71 restricting head |
| 9 anus | 81, 82, 83 screws |
| 31 outer tube | 91 rectum |
| 32 tube body | 92 large intestine |
| 33 retaining groove | |

I claim:

1. A sutureless, intestinal anastomosis gun for an anastomosis ring, comprising:

a housing comprising an outer tube portion having first and second ends and a tube body portion having first and second ends, the first end of the outer tube portion being connected to the first end of the tube body portion, and being larger in diameter than the tube body portion, and the tube body portion being longer in length than the outer tube portion;

a guide head in the shape of a smooth conic housing fitted over the second end of the outer tube portion for inserting into the rectum through the anus;

a nut mounted on the second end of the tube body portion opposite the outer tube portion;

a lining tube having an upper end and a lower end, the lining tube being fitted inside the outer tube portion, the upper end of the lining tube being adjacent to the second end of the outer tube portion and being formed into a stop edge;

a filler plate threaded at the lower end of the lining tube;

an anastomosis ring seat having an upper end and a lower end, the lower end being formed into a flange for mounting in the lining tube and the upper end being divided into a number of segments by the same number of grooves, such that the diameter of the upper end of the ring seat can be altered;

a spring mounted between the flange and the filler plate in the lining tube;

a movable shaft mounted in the housing and having upper and lower ends, the upper end extending through the filler plate and the lower end being connected to the lower end of the anastomosis ring seat, the movable shaft being provided with an elongated slit;

a fixed shaft mounted in the movable shaft and having upper and lower ends, the lower end of the fixed shaft being affixed to the outer tube portion and the upper end of the fixed shaft forming a restricting head so as to restrict the size of the upper end of the anastomosis ring seat;

a screw rod located in the tube body portion and having upper and lower ends, the upper end being connected to the movable shaft and the lower end being threaded to the nut;

whereby, in use, intestinal anastomosis can be performed by threading a screw through the elongated slit of the movable shaft to the fixed shaft therein, thus allowing linear movement, so that during operation, when the nut is rotated, the lining tube is retracted relative to the outer tube portion and then the anastomosis ring seat is retracted relative to the lining tube under the action of the spring, so as to push the end of the rectum into the gap of the anastomosis ring, whereafter the anastomosis ring is snapped closed and the gun is then disengaged from the anastomosis ring.

* * * * *